United States Patent [19]

Crow

[11] Patent Number: 5,423,798
[45] Date of Patent: Jun. 13, 1995

[54] OPHTHALMIC SURGICAL LASER APPARATUS

[76] Inventor: Lowell M. Crow, 629 Park Hill Rd., Danville, Calif. 94526

[21] Appl. No.: 719,073

[22] Filed: Jun. 21, 1991

Related U.S. Application Data

[63] Continuation of Ser. No. 473,132, Jan. 29, 1990, abandoned, which is a continuation of Ser. No. 184,084, Apr. 20, 1988, abandoned.

[51] Int. Cl.⁶ ............................................. A61N 5/06
[52] U.S. Cl. ........................................ 606/4; 606/3; 606/10; 606/15
[58] Field of Search ................. 128/395, 397, 398; 372/69, 70, 75; 606/2, 4–6, 10, 13–16, 3

[56] References Cited

U.S. PATENT DOCUMENTS

| | | | |
|---|---|---|---|
| 3,315,680 | 4/1967 | Silbertrust . | |
| 3,348,547 | 10/1967 | Kavanagh . | |
| 3,982,541 | 9/1976 | L'Esperance, Jr. | 606/14 |
| 4,082,423 | 4/1978 | Glista et al. | 385/103 |
| 4,653,056 | 3/1987 | Baer | 372/27 |
| 4,732,460 | 3/1988 | Kele et al. | 128/303.1 |
| 4,854,315 | 8/1989 | Stack et al. | 606/15 |
| 4,911,712 | 3/1990 | Harrington | 606/14 |

FOREIGN PATENT DOCUMENTS

198959 10/1986 European Pat. Off. ......... 128/303.1

OTHER PUBLICATIONS

Wolbarsht, et al., "Laser in Opthalmology: The Path from Theory to Application", *Applied Optics,* vol. 18, No. 10, pp. 1518–1526, (1979).
Wolbarsht, et al., "The Rationale of Photocoagulation Therapy for Proliferation Diabetic Retinopathy: A Review and Model", *Ophthalmic Surgery,* vol. 11, No. 4, pp. 235–245 (1980).
Landers, et al., "Panretinal Photocoagulation and Retinal Oxygenation", *Retina,* 2:167-175 (1982).
Fejer, et al., "Laser Assisted Growth of Optical Quality Single Crystal Fibers", *SPIE,* vol. 460, pp. 26–32 (1984).
Fejer, et al., "Laser-heated Miniature Pedestal Growth Apparatus for Single-Crystal Optical Fibers," *Rev. Sci. Instrum.,* 55:11, pp. 1791–1796, (1984).
Wolbarsht, et al., "4.2 Pars Plana $CO_2$ Laser Vitrectomy", *Docum. Ophthal. Proc. Series,* vol. 36, pp. 259–264 (1984).
Esterowitz, et al., "Mid-IR Solid State Laser with Fiber Optics as an Ideal Medical Scalpel," *Proc. of the International Conf. on Lasers,* pp. 68–71 (1985).
Esterowitz, et al., "Angioplasty with a Laser and Fiber Optics at 2.94 μm", *SPIE Optical and Laser Technology in Medicine,* vol. 605, pp. 32–36 (1986).
Sternberg, jr., et al., "Contact Lens Filter for Macular Photocoagulation with Monochromatic Green Argon Laser," *Retina,* 6:164–168 (1986).
Wolbarsht, "New Thoughts on Vitreous Surgery," *Lasers in Ophthalmology,* vol. 1, No. 2, pp. 73–81 (1986).
T. M. Quist, et al, Applied Physics Letters, 1, 91 (1962).
G. J. Kintz, et al, Applied Physics Letters 50 (22) 1 Jun., 1987.
T. Y. Fan, et al, Technical Digest, Conf. on Lasers and ElectroOptics, 26 Apr.–1 May 1987, Baltimore, Md.
E. V. Zharikov, et al, (Moscow) 1, 1867(1974), Soviet Journal of Quantum Electronics, 4, 1039 (1974).
R. N. Hall, et al, Physics Review Letters, 9 366 (1962).
M. I. Nathan, et al, Applied Physics Letters, 1 62, (1962).
F. A. l'Esperance, Jr., et al, British Journal of Ophthalmology vol. 53, No. 5:310-322, May 1969.
M. L. Wolbarsht, Lasers in Ophthalmology, vol. 1, No. 2, 1986.
M. J. F. Digonnett, et al, Applied Optics, 24, 3 (1985).
L. Esterowitz, Topical Meeting on Tunable Solid State Lasers, Oct. 26–28, 1987, Williamsburg, Va.
C. A. Puliafito, et al, Archives of Ophthalmology, vol. 105: 424–427, Mar. 1987.

*Primary Examiner*—David M. Shay
*Attorney, Agent, or Firm*—Bogle & Gates

[57] ABSTRACT

A solid-state ophthalmic surgical laser operating in the near and mid-infrared region (approximately 0.8 and 2.94 μm) comprises a YAG laser including a trivalent erbium activator (Er:YAG) which is pumped by a semiconductor laser diode array. Either the pump wavelength (0.8 μm) or the wavelength from the Er:YAG (2.94 μm) can be alternately selected by the user for performing photocoagulation or photoablative surgical procedures on or within the eye. A single crystal sapphire fiberoptic delivery system transmits either wavelength to the surgical site.

12 Claims, 2 Drawing Sheets

OPHTHALMIC SURGICAL LASER APPARATUS

This is a Continuation of application Ser. No. 07/473,132, filed Jan. 29, 1990, which is a continuation of Ser. No. 184,084 filed Apr. 20, 1988, now abandoned.

BACKGROUND—FIELD OF THE INVENTION

This invention relates to solid state lasers and more particularly to solid state lasers operative in the near and mid-infrared spectrum. The present invention relates generally to an ophthalmic surgical apparatus employing an operating laser generator for cutting or ablating tissues and a semiconductor laser which is used to pump the former and which can also be used independently for photocoagulation of various structures of the eye.

BACKGROUND—DESCRIPTION OF THE PRIOR ART

Several divalent and trivalent rare-earth ions incorporated in various host crystals have been found to exhibit stimulated emission in the near infrared. This class of solid state lasers, which is based on vibronic transitions in rare earth ions has been extensively reported in the scientific literature up to this date. Generation of laser radiation in the 3 μm wavelength range in yttrium aluminum garnet (YAG) crystals activated with erbium ions was first reported by E. V. Zharikov, et al, (Moscow) 1, 1867 (1974), *Soviet Journal of Quantum Electronics* 4, 1039 (1974).

Early experiments with semiconductor laser diodes were reported in the scientific literature by three groups in the early 1960's with the following publications: R. N. Hall, et al, "Coherent Light Emission from GaAs Junctions," *Physical Review Letters*, 9, 366 (1962), M. I. Nathan, et al, "Stimulated Emission of Radiation from GaAs p-n Junction," *Applied Physics Letters*, 1, 62 (1962), and T. M. Quist, et al, "Semiconductor Maser of GaAs," *Applied Physics Letters*, 1, 91 (1962).

The standard approach for exciting solid state lasers is to use broadband incoherent sources to pump the energy levels in rare-earth, transition metal or actinide activator ions. More recently, semiconductor laser diodes have been used to pump solid state lasers which is described in U.S. Pat. of Baer and Keirstead U.S. Pat. No. 4,653,056. In 1987, several research groups reported the pumping of several types of solid state lasers with semiconductor laser diodes. G. J. Kintz, R. Allen, and L. Esterowitz in their paper titled "cw and pulsed 2.8 μm laser emission from diode-pumped $Er^{3+}$:LiYF$_4$ at room temperature," *Applied Physics Letters* 50 (22) 1 Jun. 1987, reported laser emission from an erbrium-doped yttrium lithium fluoride (LiYF$_4$) crystal (Er:YLF) pumped by a laser diode array. Since each individual diode is quite small, it becomes necessary to closely pack a plurality of individual diodes into arrays in order to generate the required amounts of input power to the larger pumped solid-state laser rod. T. Y. Fan, G. Huber and R. L. Byer reported on a "Continuous-wave diode-laser-pumped 2-μm Ho:YAG laser at room temperature," Technical Digest, Conference on Lasers and Electro-Optics, 26 Apr.-1 May 1987, Baltimore, Md. At the same conference, diode pumping of Nd:YAG, $Er^{3+}$:YLF as well as other crystals was also reported. Later in 1987, L. Esterowitz reported on "Recent Developments in Diode Pumped Rare Earth Lasers," Topical Meeting on Tunable Solid State Lasers, Oct. 26–28, 1987, Williamsburg, Va., wherein it was reported that under diode pumping, room temperature laser operation was observed at 2.9 μm in erbium ions in both YAG and YLF matrices.

None of these prior art devices is capable of producing satisfactory results in a practical and highly flexible instrument which can be effectively used by a surgeon for micro-surgery on living tissue or tissue substructures of the eye.

C. A. Puliafito, et al. in their paper titled "Semiconductor Laser Endophotocoagulation of the Retina," *Archives of Ophthamology*, Vol. 105, pages 424–427, March 1987, reported on the use of a semiconductor diode array laser emitting near 800 nm utilizing an optical fiber intraocular probe to perform retinal photocoagulation (endophotocoagulation). This device is a single purpose laser system for endophotocoagulation and does not address cutting or ablating vitreal membranes.

The process of photocoagulation is commonly used by ophthalmic surgeons to coagulate proliferating blood vessels caused by diabetic retinopathy, to repair detatched retinas by fusing the retina and the choroid, and to destroy tumors in the eye. In these applications, a laser beam is focused on the retina and, by short exposures of radiation, it produces a pinpoint thermal coagulation lesion on the retina or retinal substructure. Typical devices for use in such operations are disclosed in U.S. Pat. of Silbertrust et al. U.S. Pat. No. 3,315,680, and Kavanagh U.S. Pat. No. 3,348,547, and in the article by F. A. l'Esperance, Jr., et al., "Photocoagulation Delivery Systems For Continuous-wave Lasers," *British Journal of Ophthalmology*, Vol. 53, No. 5, Pages 310–322, May, 1969. Prior to the above mentioned report by Puliafito et al., the process of photocoagulation and endophotocoagulation was performed almost exclusively with argon ion lasers emitting at 488 and 514 nm and argon ion pumped dye lasers operating in the visible spectrum.

In another form of eye pathology, dealing with the gel-like vitreous of the eye, it is sometimes necessary to remove this material in a procedure called vitrectomy. Removal of the vitreous is often complicated by relatively tough membraneous strands attached to the retina. Removal of the vitreous and its associated membranes from the eye is a difficult and delicate surgical procedure, and mechanical disturbances of these strands will tear the retina. One of the most important and delicate parts of modern vitreoretinal surgery is dissection of the various tissue planes. These can vary from fibrous and/or fibrovascular vitreous membranes to preretinal, subretinal, retrolental, or pupillary membranes. The objective of surgery is to relieve tangential retinal traction and micro-scissors and a variety of mechanical instruments are normally used for segmentation or delamination of tissues. Aggressive mechanical membrane dissection, however, is associated with a significant risk of retinal hole formation and subsequent vision deficits. An alternative and a non-mechanical approach to this delicate form of surgery was proposed by M. L. Wolbarsht in an article titled "New thoughts on vitreous surgery," *Lasers in Ophthalmology* Vol. 1, No. 2, pages 73–81, 1986. The laser removal of the vitreous is reserved for those portions of the vitreous which have strands attached to the retina or when sensitive structures, such as the retina, are approached. The surgical field is viewed through the cornea with an operating microscope. Wolbarsht proposed the use of the Er:YAG operating at the 2.94 μm wavelength for this procedure. This wavelength is at the peak of water absorption and, therefore, biological tissue, and has a very high tissue absorption coefficient. With a limited absorption depth of approximately 1 μm, the Er:YAG provides high tissue absorption with minimal thermal diffusion to surrounding tissues. This is optimal for vitreal surgery. To minimize the opportunity for thermal diffusion, it is desirable to limit the absorption depth to the thinnest layer nearest the surface in order to ablate the superficial material without disturbing underlying tissues. The 294 μm wavelength is ideal when this surgical objective is present.

Retinal endophotocoagulation following vitrectomy or lensectomy is often required and has several advantages over conventional slit lamp delivery of laser energy. In the latter, the patient is brought to the argon laser photocoagulator with a slit-lamp delivery system as soon as feasible after the operation. This procedure is often complicated by eye movement and poor patient cooperation. The cornea often becomes hazy and the vitreous itself may become slightly cloudy. Furthermore, visibility of the retina may be poor, such as following hemorrhage into the vitreous or when the retina is detached. It is preferable to perform retinal endophotocoagulation around retinal breaks or retinotomy sites during the operation and to perform panretinal photocoagulation for proliferative diabetic retinopathy immediately following vitrectomy. Therefore, most ophthalmic surgeons would find it desirable to perform laser vitrectomy and endophotocoagulation with the same laser system without having to change from one laser to another, and exchange one fiberoptic probe for another. The present invention provides the ophthalmic surgeon with the flexibility to rapidly alternate between the endophotocoagulation wavelength and the photoablation wavelength; through the same fiberoptic delivery system. This flexibility relieves the surgeon from the burden of introducing separate coagulation and ablation instrumentation into the surgical field and from repositioning the optical fiber. The net effect is a reduction of instrumentation needed for the operating procedure, decreased operating time and, it enables the surgeon to rapidly coagulate bleeding sites thereby reducing blood loss into the eye.

The 294 μm wavelength of the Er:YAG, while ideal for dissection of vitreal membranes, is not suitable for retinal photocoagulation as it will destroy surface structures of the retina and produce undesired effects. Conversely, the 800 nm region of the semiconductor laser does not have a high water/tissue absorption coefficient and is not suitable for photoablation of vitreal membranes; but has demonstrated utility for retinal photocoagulation. To perform both types of laser surgery during the course of one operation, two separate lasers would be required. Until the present time, no device or method has been proposed to combine a semiconductor pump laser with the Er:YAG laser and provide the delivery of either wavelength therefrom, at the option of the user, for the purposes of performing dissection or photoablation of ocular tissues and photocoagulation. Examples of additional types of ocular surgery that may be undertaken with this invention include corneal surgery, pupillary cataract removal and tumor removal.

The fiberoptic delivery system used in laser vitreoretinal surgery must be compatible with other instruments used in vitreous surgery. Generally, this would limit the outside diameter of the optical delivery system to between 1.5 mm and 2.0 min. Prior art devices have heretofore been of limited use due to the lack of a fiberoptic material that efficiently transmits the 294 μm wavelength. The fiberoptic material must be of sufficiently small profile to be compatible with other vitreous surgery instruments and, function in either a fluid-filled or gas-filled eye. The present invention utilizes small profile single crystal optical fibers of sapphire produced by LaserGenics Corporation of San Jose, Calif. This material has a very broad transmission bandwidth and efficiently transmits optical energy from both the laser diode array and the Er:YAG laser.

BACKGROUND OF THE INVENTION

This invention relates to solid state lasers which are optically pumped by semiconductor laser diodes, and, in particular, to the trivalent erbium doped yttrium aluminum garnet, $Er^{3+}$:YAG laser, that has a laser transition at precisely 2.94 μm. The lasing element selected for use in a specific rare-earth doped laser crystal is an ion whose absorption in the host crystal takes place in the region of the laser diode pump wavelength. The gain medium is formed by use of any well-known crystal growth process. Such methods are well-known in the crystal growth art and it is believed not necessary to set forth the complete process herein.

The concept of a dual purpose, multi-wavelength ophthalmic surgical laser comprised of a semiconductor laser diode array used to optically pump a high energy gain medium such as erbium doped YAG has not been proposed until this time.

Continuous wave GaAlAs laser diode arrays emitting near the 800 nm region with greater than one watt of output power are available from Spectra Diode Laboratories, Palo Alto, Calif. and the Sony Corporation, Cypress, Calif. The semiconductor laser array is mounted on a base which is thermoelectrically cooled as shown in FIG. 1. The output energy of the diode array is directed into the gain medium by the use of well-known coupling optics as depicted in FIG. 1. The energy storage of the Er:YAG is determined by its upper laser lifetime which is 4.5 microseconds. Because the lower laser level has a lifetime of 9 microseconds, the pulse repetition rate is limited to less than approximately 50 Hz.

The ablation of vitreal membranes while minimizing thermal damage to adjacent tissues is limited by the time required for heat diffusion. The phase change from water to steam, without appreciable heating of adjacent tissues is reached when the laser exposure duration is less than the thermal diffusion or relaxation time. For the 2.94 μm wavelength and an absorption depth of 1 μm, the optimum laser pulse width is approximately 1.3 microseconds. The optimum laser pulse energy for a 300 μm spot size is approximately 220 microjoules. To achieve this pulse energy level, the diode array will have an output power of 700 milliwatts although a one watt array or greater is preferred. The complete laser system is comprised of a semiconductor laser diode array, coupling optics, a sensitized Er:YAG laser rod, an acousto-optic Q-switch, an output coupler and fiberoptic delivery system, power supply, energy monitoring system, and energy control and safety subsystem.

OBJECT AND SUMMARY OF THE INVENTION

An object of this invention is to provide a method of optical pumping of an erbium laser whereby energy from a semiconductor laser array excitation light source is utilized effectively and a laser beam of wavelength of 2.94 μm is emitted with high efficiency; and of such character that it can operate pulsed (Q-switched).

Another object of this invention is to provide new and improved lasers in which the operator can alternate the output wavelength between that of the pump semiconductor laser array and the gain medium which is pumped by the semiconductor laser array.

Still yet another object of this invention is to provide new and improved lasers whose optical output, either from the semiconductor pump laser or from the laser pumped by the semiconductor laser can be delivered through a single fiberoptic and be used for ocular surgery as well as for surgery elsewhere in the body, or for industrial and scientific applications.

Figure 1:
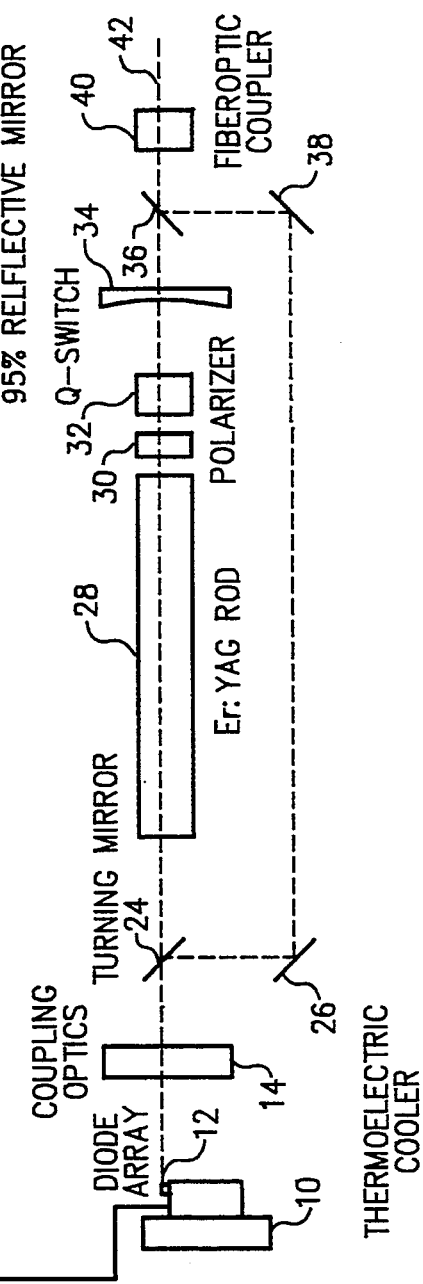
FIG. 1 shows an overall schematic illustration of the multi-wavelength laser system.

DRAWING REFERENCE NUMERALS 8. power supply
10. thermoelectric cooler
12. semiconductor laser diode array
14. coupling optics
16. collimating lens
18. anamorphic prism
20. anamorphic prism
22. focusing lens
24. turning mirror
26. turning mirror
28. Er:YAG rod
30. polarizer
32. Q-switch
34. 95% reflective mirror
36. turning mirror
38. turning mirror
40. fiberoptic coupler
42. fiberoptic

DETAILED DESCRIPTION OF THE INVENTION

Figure 2:
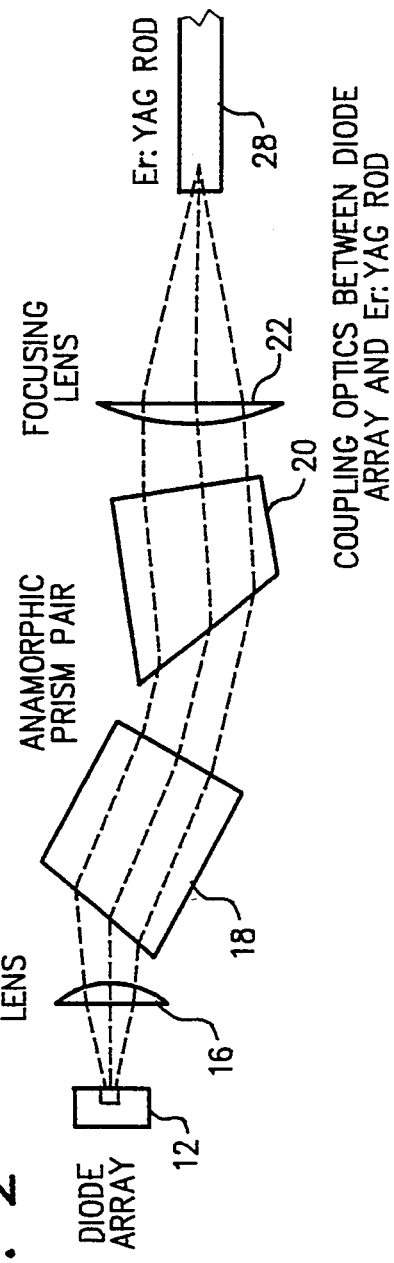
FIG. 2 shows the tip view of the coupling optics between the diode array and the Er:YAG rod.
Figure 3:
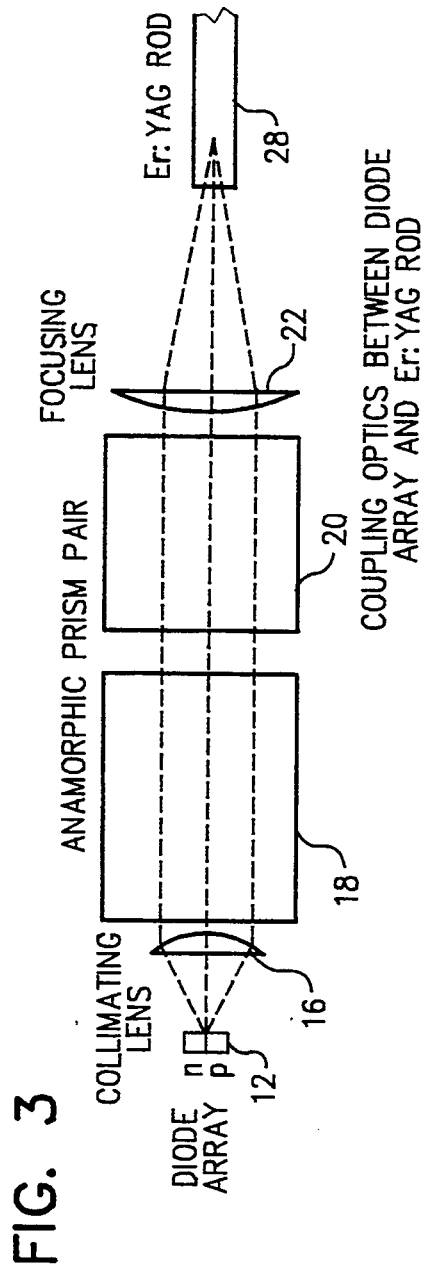
FIG. 3 shows the side view of the coupling optics between the diode array and the Er:YAG rod.
Figure 4:
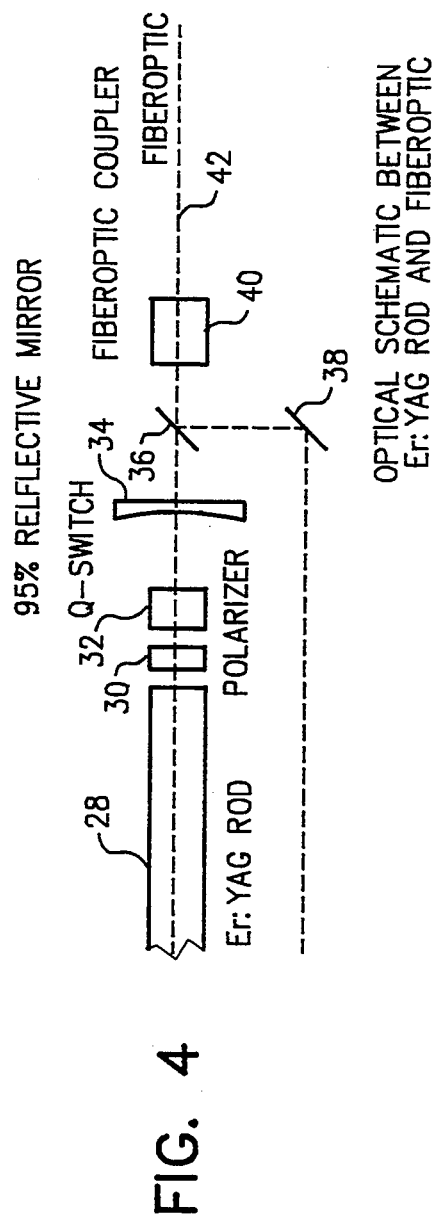
FIG. 4 shows a schematic illustration of the optical path and components between the Er:YAG rod and the fiberoptic delivery system.

FIG. 1 is a simple laser system powered by 50 or 60 Hz current controlled by a standard power supply 8 delivering electrical energy to a semiconductor laser diode or diode array 12 which is cooled by a thermoelectric cooler 10. The cooler is used to cool the diode and adjust the diode array emission spectrum to the absorption band of the Er:YAG laser rod 28. The pump source wavelength is chosen so that it can both resonantly pump the lasing element and, be useful as an ophthalmic photocoagulator light source. The laser diode array output is directed through a conventional set of coupling optics 14 which is shown in more detail in FIG. 2 and 3. The coupling optics are comprised of a collimating lens 16, two anamorphic prisms 18, 20 and a focusing lens 22 which shapes the pump beam to the mode of the optical resonator.

The coupling optics will focus the output from the laser diode pump into the laser rod. The optimum signal pump waist radius has been calculated by M. J. F. Digonnet and C. J. Gaeta, "Theoretical analysis of optical fiber laser amplifiers and oscillators," *Applied Optics*, 24, 3 (1985), to be $$W_{s,p} = \left( \frac{\lambda_{s,p} l_{YAG}}{\sqrt{3} \, \pi n} \right)^{\frac{1}{2}}$$

where $\lambda_{s,p}$ is the signal or pump wavelength, $l_{YAG}$ is the length of the laser rod, and n is the refractive index of the laser rod. For a pump wavelength of 790 nm and a crystal length of 1 cm we have that $W_p \approx 2.8 \times 10^{-3}$ cm and for a signal wavelength of 2.94 μm we have that $W_s \approx 5.45 \times 10^{-3}$ cm. From this value, the optimum resonator giving the lowest threshold and the maximum output power and efficiency can be developed.

When the resonator is formed by the plane mirror on the end of the Er:YAG rod 28 and the curved mirror 34 as shown in FIG. 1 then the TEM$_{00}$ spot size at the plane mirror is given by $W_s = \sqrt{\lambda_s/\pi} [L(R-L)]^{\frac{1}{4}}$ where R is the concave mirror radius and L is the effective cavity length given by $L = (l_{YAG}/n_{YAG}) + l_{air} + (l_{mod}/n_{mod})$. For a 5 cm cavity length and one cm modulator we have that L=4.2 cm. From this we obtain a radius of curvature for the output coupler 34 of R=4.22 cm or very near to concentric. In order to increase the stability of the system while sacrificing slightly in the output power, a good compromise would be a mirror radius of curvature of 5 cm. For this case $W_s^2 = 13.1 \times 10^{-3}$ cm and the average single mode radius in the laser rod is given by $$\overline{W_s^2} = W_s^2 \left[ 1 + \frac{l_{YAG}^2}{3} \left( \frac{\lambda_s}{\pi n_{YAG} W_s^2} \right)^2 \right]$$

Therefore, $\overline{W_s^2} = 1.77 \times 10^{-4}$ cm$^2$.

The pump power threshold is given by:

$$P_{TH} = \frac{h\nu_p}{\sigma \tau_f} \frac{\delta}{2} \left[ \frac{\pi}{2} (\overline{W_p^2} + \overline{W_s^2}) \right]$$

when $\nu_p$ is the pump frequency, $\sigma$ is the net-gain cross section, $\tau_{fl}$ is the fluorescence lifetime and $\delta$ is the round trip cavity loss including output coupling. For a pump spot size smaller than the signal mode size (our case) the output power can be written as:

$$P_{out} = \frac{T}{\delta} \frac{\lambda_p}{\lambda_s} (P_{abs} - P_{TH})$$

where T is the transmission of the output coupler and $P_{abs}$ is the absorbed pump power. As the losses in the laser rod and other optical elements are small we can write $\delta$ as: $\delta = S + T = 2(N-1)s + T$ where S is the round trip loss due to surface scattering, N is the total number of surfaces in the cavity and s is the average scattering loss per surface; this is typically 0.25% or less. Therefore, for the cavity shown in FIG. 1 $S \approx 12 \times 0.0025 = 0.03$. Therefore, $$P_{out} = \frac{T}{T + 0.03} \frac{\lambda_p}{\lambda_s} (P_{abs} - P_{TH}).$$

The only other parameter that needs to be set is the transmission of the output coupler, T. The output power and efficiency are not strong functions of T. The optimum value of T can be determined from our expression of $P_{out}$. Letting the derivative of $P_{out}$ with respect to T equal zero and solving for T we obtain for the optimum value of T the expression $$T_{opt.} = \left[ \frac{4\lambda_p \sigma \tau_f S P_{abs.}}{\pi \zeta c (W_p^2 + W_s^2)} \right]^{\frac{1}{2}} - S$$

Using our values that we determined above for $W_p^2$ and $W_s^2$ and the values of $\sigma$ and $\tau_f$ for erbium doped YALO (yttrium aluminum oxide) we obtain $$T_{opt.} = 0.14 \sqrt{P_{abs}} - 0.03$$

Using a commercial one watt laser diode array and assuming 500 milliwatts can be coupled into the laser crystal and absorbed we have that:

$$T_{opt.} = 6.9\%$$

We than have that $\delta = 0.099$ and the threshold power from this device will be:

$$P_{TH} = 155 \text{ mW}$$

and the output power will be:

$$P_{out} = \frac{T}{\delta} \frac{\lambda_p}{\lambda_s} (P_{abs} - P_{TH}) = 65 \text{ mW}$$

Turning mirrors 24, 26, 36 and 38 are used to direct the pump radiation around the Er:YAG rod and to bypass the Er:YAG and to be used as a photocoagulator, at the option of the laser operator. When not activated, turning mirrors 24 and 36 will allow conventional pumping of the Er:YAG optical resonator. The resonator is formed by the back face of the Er:YAG rod (the end nearest the coupling optics) which has an anti-reflective (AR) coating to match the diode array pump wavelength plus a high reflective coating (HR) to match the 2.9 μm wavelength of the Er:YAG and the 95% reflective mirror 34. The opposite end of the Er:YAG rod (the end nearest the focusing mirror) is AR coated for the output wavelength of the Er:YAG laser of 294 μm.

It has been determined that laser elements suitable for cascade laser action are those rare-earth doped solids in which the rare-earth element serves as an activator and the host matrix may be selected from oxide, glass, or fluoride hosts. It is therefore possible to make active laser elements from activator ions such as holmium, Ho or neodymium, Nd. Correspondingly, the diode array pump source may also vary in wavelength to match the absorption band(s) of the gain medium.

The Q-switch 32 is a standard acousto-optic or electro-optic shutter for interrupting the optical beam within the laser cavity to store or accumulate energy for the purpose of producing short optical pulses of high peak powers. The electro-optic shutter requires a polarizer 40 in the laser cavity. The mode of operation of this device is well-known and documented in the art.

The reflective mirror 34 operates in a conventional way by reflecting photons back and forth within the laser cavity while allowing a portion to exit the laser cavity.

The fiberoptic coupling device 40 is of a type which is standard technology and well-known in the art. This device comprises standard optical elements for focusing the light exiting the laser cavity into the polished face of the fiberoptic 42.

The fiberoptic is made of single crystal sapphire, a material which is transparent to both wavelengths of the laser system, e.g. ≈800 nm of the diode array and 2.94 μm of the Er:YAG. Other fiberoptic materials which are efficiently transmissive and function well in the described surgical environment could also be used.

Obviously many modifications and variations of the present invention are possible in light of the above teachings. It is therefore to be understood that within the scope of the appended claims the invention may be practiced otherwise than as specifically described.

OPERATION OF INVENTION

The multi-wavelength ophthalmic laser of FIG. 1 will perform several delicate ocular and intraocular surgical procedures such as dissecting vitreal membranes, retinal photocoagulation, corneal surgery, tumor removal and pupillary cataract removal.

Prior to ophthalmic surgery, the patient and the operating theater should be prepared according to established operating procedures. The fiberoptic 42 should be sterilized prior to the start of surgery. In the case of intraocular surgery and in particular, vitrectomy, the user may elect to use this invention in either a fluid-filled or gas-filled eye, depending on the judgement and experience of the ophthalmic surgeon. The removal of the vitreous from within the eye is one of the most delicate surgical procedures. The structures are very small and the tissues are extremely weak. The retina, for example, has been described as having the strength and consistency of wet facial tissue. Accompanying this high degree of fragility is the fact that small damage spots in the retina may cause large vision deficits.

The operating site is visualized through the cornea with the assistance of an operating microscope. Surgical instruments such as vitreous cutter, micro-scissors, optical fibers for illumination, infusion and drainage lines, etc. are inserted through pressure-tight holes in the pars plana. The normal internal pressure of the eye is maintained. The laser removal of the vitreous is reserved for those portions of the vitreous which have strands attached to the retina or when approaching sensitive structures, such as the retina. Since the 294 μm wavelength of the Er:YAG is at the peak of water absorption, there are differences in the surgical approach depending on whether the eye is fluid-filled or gas-filled. In the case of the latter, the ophthalmic surgeon may elect to use a contact or non-contact approach with the sterilized fiberoptic 42.

The ophthalmic laser depicted in FIG. 1 is turned on by activation of the power supply 8 and the primary wavelength of the Er:YAG is selected by the user. In this case, turning mirrors 24 and 36 are automatically positioned so as to allow the pump radiation from the laser diode or diode array 12 to pass through to the Er:YAG rod 28 which produces the 294 μm wavelength output which exits the fiberoptic 42. In this operating mode, the Q-switch 32 is activated so as to produce high peak power pulses at high repetition rates. The fiberoptic 42 is inserted in the eye through the port previously established for introducing surgical instruments. If the contact approach is preferred, the tip of the fiberoptic 42 should be carefully and gently placed in contact with the vitreal membranes to be dissected and laser power applied gradually up to the desired level. Due to the high water absorption of the 294 μm wavelength, the contact approach is necessary in the fluid-filled eye while either the contact or non-contact approach can be used in the gas-filled eye. When the non-contact approach is used, the fiberoptic 42 should be advanced to within approximately one millimeter of the target tissue then laser energy should be applied as described above.

It is often desirable and necessary to perform endophotocoagulation during or immediately following vitrectomy or lensectomy. Endophotocoagulation around retinal breaks or retinotomy sites and panretinal photocoagulation is accomplished with the use of the wavelength from the diode array 12 (secondary wavelength). When the operator makes the secondary wavelength selection, turning mirrors 24 and 36 are automatically activated so as to reflect the secondary wavelength, bypassing the Er:YAG rod 28, the polarizer 30, the Q-switch 32, and the 95% reflective mirror 34. The secondary wavelength is directed to the fiberoptic coupler 40 and exits the fiberoptic 42. This wavelength operates in a continuous-wave manner, as it is driven by the DC power supply 8. A non-contact approach is preferred for this procedure but the contact approach may also be used. The ophthalmic surgeon advances the fiberoptic 42 to within approximately one millimeter of the target tissue and applies the desired level of laser energy in the manner previously described.

The integration of a semiconductor laser diode array pump laser with a crystalline or glass medium doped with erbium ions, provides an efficient multi-wavelength laser system that is small and simple to manufacture, and which makes it possible for the ophthalmic surgeon to perform photocoagulation and ablative surgical procedures on or within the eye with a single fiberoptic and within one operating procedure. Furthermore, this invention possesses important advantages in cost, weight, size, power consumption, reliability, and ease of operation. Its small size and power requirements make it an especially desirable candidate for portable applications.

What is claimed is:

1. A solid state ophthalmic surgical laser apparatus having a first output wavelength and a second output wavelength, including means for photocoagulation comprising said first output wavelength, and means for photoablation comprising said second output wavelength, and wherein said means for photoablation comprises an Er:YAG laser and said means for photocoagulation comprises a semiconductor laser and having a single fiber-optic delivery system, said single fiber-optic delivery system being a sapphire optical fiber and configured to permit contacting a surgical site with said fiber-optic, to deliver both said first output wavelength and said second output wavelength to the surgical site.

2. A solid state ophthalmic surgical laser apparatus having a first output wavelength and a second output wavelength, including means for ophthalmic photocoagulation comprising said first output wavelength and means for ophthalmic photoablation comprising said second output wavelength, wherein said means for photoablation comprises a first pumpable laser, and wherein said means for photocoagulation comprises a second laser, said second laser being also usable for pumping said first pumpable laser, said first laser emitting radiation suitable for ophthalmic photoablation at about the 2.94 micron wavelength region, said second laser emitting radiation suitable for photocoagulation at about 800 nm; and having a single fiber-optic delivery system, said single fiber-optic delivery system being configured to permit contacting a surgical site with said fiber-optic to deliver both said first output wavelength light and said second output wavelength light to the surgical site.

3. The invention as claimed in claim 1 wherein said second laser comprises a semiconductor laser diode array with an output of about 800 nm.

4. A solid state ophthalmic surgical laser as claimed in claim 1 further comprising means for selecting the desired output wavelength.

5. A solid state ophthalmic surgical laser, as claimed in claim 1, wherein said first laser comprises an Er:YAG crystal.

6. A solid state ophthalmic surgical laser as claimed in claim 1, wherein said fiber-optic delivery system comprises sapphire optical fibers.

7. A method for ophthalmic laser surgery comprising:
providing a first pumpable laser for emitting laser radiation in a first wavelength of about 2.94 microns;
providing a second laser for emitting laser radiation at a second wavelength of about 800 nm;
providing a single fiber optic delivery system;
photocoagulating ocular tissue using said second laser;
pumping said first pumpable laser using said second laser;
photoablating ocular tissue using said first laser; and
delivering both said first wavelength radiation and said second wavelength radiation to a surgical site using said single fiber-optic delivery system to contact the surgical site with said fiber-optic.

8. A method for ophthalmic surgical laser as claimed in claim 7, wherein said step of providing a fiber-optic delivery system comprises providing sapphire optical fibers.

9. A method, as claimed in claim 8, further comprising selecting laser radiation emitted from said second laser for use either in said step of pumping said pumpable laser or in said step of photocoagulating.

10. A method, as claimed in claim 8, wherein said step of providing said first pumpable laser comprises providing an Er:YAG laser.

11. A method, as claimed in claim 10, wherein said step of providing said second laser comprises providing at least a first semiconductor laser diode.

12. A method for ophthalmic laser surgery comprising:
providing a first pumpable laser for emitting laser radiation in a first wavelength of about 2.94 microns;
providing a second laser for emitting laser radiation in a second wavelength of about 800 nm;
providing a single fiber optic delivery system;
photocoagulating ocular tissue using said second laser;
pumping said first pumpable laser using said second laser;
photoablating ocular tissue using said first laser;
delivering both said first wavelength radiation and said second wavelength radiation to a surgical site using said single fiber-optic delivery system to contact the surgical site with said fiber-optic; and
wherein said step of providing a fiber-optic delivery system comprises providing single crystal sapphire fibers.

* * * * *